United States Patent
Richardson

(10) Patent No.: US 9,427,195 B1
(45) Date of Patent: Aug. 30, 2016

(54) MOBILE EMERGENCY VEHICLE WITH COMPUTERIZED TOMOGRAPHY SCANNER

(71) Applicant: FRAZER, LTD., Houston, TX (US)

(72) Inventor: Thomas A. Richardson, Houston, TX (US)

(73) Assignee: FRAZER, LTD., Houston, TX (US)

(*) Notice: Subject to any disclaimer, the term of this patent is extended or adjusted under 35 U.S.C. 154(b) by 0 days.

(21) Appl. No.: 14/631,475

(22) Filed: Feb. 25, 2015

(51) Int. Cl.
*A61B 6/03* (2006.01)
*A61B 6/00* (2006.01)
*A61B 6/04* (2006.01)
*A61G 3/00* (2006.01)

(52) U.S. Cl.
CPC ............ *A61B 6/035* (2013.01); *A61B 6/0407* (2013.01); *A61B 6/4405* (2013.01); *A61G 3/001* (2013.01)

(58) Field of Classification Search
CPC ........ A61B 6/03; A61B 6/032; A61B 6/035; A61B 6/0407; A61B 6/4405; A61G 3/001; B60P 3/14
See application file for complete search history.

(56) References Cited

U.S. PATENT DOCUMENTS

| | | | |
|---|---|---|---|
| 4,181,347 A | 1/1980 | Clark | |
| 4,230,358 A * | 10/1980 | Legueu | B60P 3/14 180/89.11 |
| 4,449,746 A | 5/1984 | Clark | |
| 4,485,504 A * | 12/1984 | Lehmann | A61G 1/044 296/20 |
| 4,523,078 A * | 6/1985 | Lehmann | A47J 39/02 219/202 |
| 4,643,476 A * | 2/1987 | Montgerard | B60P 3/14 144/286.1 |
| 4,672,296 A | 6/1987 | Griffin | |
| 4,694,481 A * | 9/1987 | Tashjian | A61B 6/4405 378/198 |
| 4,743,059 A * | 5/1988 | Legueu | A61G 10/00 280/763.1 |
| 4,785,227 A | 11/1988 | Griffin | |
| 4,980,944 A * | 1/1991 | Longman | B60S 1/40 15/250.32 |
| 5,097,497 A | 3/1992 | Deucher et al. | |
| 5,236,390 A * | 8/1993 | Young | B60P 3/14 296/19 |
| 5,615,848 A * | 4/1997 | Ceriani | B64D 9/00 244/118.5 |
| 6,446,285 B1 * | 9/2002 | Chinn | A61G 1/04 108/49 |
| 6,481,887 B1 | 11/2002 | Mirabella | |
| 6,625,252 B2 | 9/2003 | Mirabella | |
| 6,685,032 B2 * | 2/2004 | Kaufmann | F16M 11/00 211/13.1 |
| 6,916,056 B2 * | 7/2005 | Mitchell | A61G 1/0567 296/20 |
| 7,264,396 B2 * | 9/2007 | Jahrling | A61B 6/032 378/195 |
| 7,397,895 B2 | 7/2008 | Bailey et al. | |

(Continued)

FOREIGN PATENT DOCUMENTS

| | | | | |
|---|---|---|---|---|
| DE | EP 0417615 A1 * | 3/1991 | ............ | A61G 3/001 |
| GB | WO 8707566 A1 * | 12/1987 | ............ | A61G 3/001 |
| IT | EP 2446870 A2 * | 5/2012 | ............ | A61G 3/001 |

*Primary Examiner* — Joseph D Pape
*Assistant Examiner* — Paul Chenevert
(74) *Attorney, Agent, or Firm* — Egbert Law Offices, PLLC

(57) ABSTRACT

An emergency vehicle has a patient compartment and a motor, a generator cooperative with the patient compartment, and a Computerized Tomography (CT) scanner positioned in the patient compartment and connected to the generator so as to supply power to the CT scanner. The CT scanner is releasably affixed to the front wall of the patient compartment. The generator is operable independently of the motor. The front wall of the patient compartment has a receptacle affixed thereto. The CT scanner has at least one pin connector extending toward the front wall. The pin connector is releasably received by the receptacle so as to fix a position of the CT scanner against the front wall.

16 Claims, 10 Drawing Sheets

(56) References Cited

U.S. PATENT DOCUMENTS

| | | | | |
|---|---|---|---|---|
| 7,530,403 B2* | 5/2009 | Cano | ............... | A62C 27/00 169/24 |
| 7,627,915 B2* | 12/2009 | Eriksson | ............... | A61G 1/04 5/625 |
| 7,636,961 B1* | 12/2009 | Starkey | ............... | A61G 1/0565 187/234 |
| 7,648,008 B2* | 1/2010 | Ohtsuka | ............... | A61B 6/4216 188/378 |
| 8,038,347 B2* | 10/2011 | Manak | ............... | A61B 5/6887 378/189 |
| 8,333,038 B2* | 12/2012 | Bates | ............... | A47B 95/008 52/238.1 |
| 8,656,842 B1* | 2/2014 | McDonley | ............... | A47B 23/04 108/149 |
| 8,851,079 B1* | 10/2014 | Schenck | ............... | A61G 1/01 128/870 |
| 8,929,510 B2* | 1/2015 | Nishino | ............... | A61B 6/4216 378/102 |
| 9,125,611 B2* | 9/2015 | Eaves | ............... | A61B 6/4405 |
| 9,180,591 B2* | 11/2015 | McLean | ............... | A47F 5/0846 |
| 2002/0085674 A1* | 7/2002 | Price | ............... | A61B 6/032 378/122 |
| 2008/0020332 A1* | 1/2008 | Lavenda | ............... | A61B 6/4233 430/495.1 |
| 2013/0243151 A1* | 9/2013 | Shih | ............... | A61B 6/035 378/9 |
| 2015/0164447 A1* | 6/2015 | Couture | ............... | A61B 6/0421 250/370.09 |
| 2015/0208994 A1* | 7/2015 | Rapoport | ............... | A61B 6/4417 600/411 |
| 2015/0230810 A1* | 8/2015 | Creighton | ............... | A61B 17/22012 604/518 |
| 2015/0282774 A1* | 10/2015 | Lee | ............... | A61B 6/032 378/8 |

* cited by examiner

MOBILE EMERGENCY VEHICLE WITH COMPUTERIZED TOMOGRAPHY SCANNER

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to mobile emergency vehicles, such as ambulances. More particularly, the present invention relates to mobile emergency vehicles that have scanning equipment therein. In particular, the present invention relates to mobile emergency medical vehicles that are adapted to facilitate the use of a Computerized Tomography (CT) scanner in locations remote from a hospital.

2. Description of Related Art Including Information Disclosed Under 37 CFR 1.97 and 37 CFR 1.98.

Strokes are currently the third leading cause of death in the United States. Strokes are also the main cause of long-term disability. Strokes are caused by an abrupt interruption of the blood supply to the brain or spinal cord. This deprives the tissue of oxygen and resulting tissue damage. Strokes typically occurring in one of two forms: (i) hemorrhagic strokes, which occur with the rupture of a blood vessel; and (ii) ischemic strokes which occur with the obstruction of a blood vessel.

Rapid diagnosis is a key to effective stroke treatment. This is because the treatment for an ischemic stroke may be contra-indicated for the treatment for a hemorrhagic stroke. Additionally, the effectiveness of a particular treatment may be time-sensitive. More particularly, the current preferred treatment for an acute ischemic stroke, i.e. the administration of tissue Plasminogen Activator (tPA) to eliminate blood clots, is contra-indicated for a hemorrhagic stroke. Furthermore, clinical data suggests that the medication used to treat ischemic strokes is most effective if it is administered within three hours of the onset of the stroke. Current diagnosis times (the time needed to identify that the patient is suffering from a stroke and to identify the hemorrhagic or ischemic nature of the stroke) frequently exceeds this three-hour window. As a result, only a fraction of current ischemic stroke victims are timely treated with tPA.

Imaging is generally necessary to properly diagnose and treat a stroke. In particular, imaging is necessary to distinguish strokes from other medical conditions, to distinguish between the different types of strokes, and to determine appropriate treatment.

Computerized Tomography (CT) has emerged as the key imaging modality in the diagnosis of strokes. CT scanners generally operate by directing x-rays into the body from a variety of positions, detecting the x-rays passing through the body, and then processing the detected x-rays so as to build a computer model of the patient's anatomy. This computer model can then be visualized so as to provide images of the patient's anatomy. It is been determined that such CT scanning, including non-enhanced CT scanning, CT angiography scanning, and CT perfusion and scanning is able to provide substantially all of the information needed to effectively diagnose and treat a stroke.

Unfortunately, the CT scanner is typically located in the hospital's radiology department and the patient is typically received in the emergency room. As such, there will be a round-trip time between the emergency room and the radiology department. This can involve substantial delays, even in the best of hospitals. As a result, the time spent in transporting the patient from the emergency room to the radiology department and then back again can consume critical time which can compromise proper treatment of the patient.

Thus, there was an urgent need for a new and improved CT scanner that is particularly well suited for use in stroke applications. As a result of this need, a mobile computerized tomography imaging system was developed by NeuroLogic Corp. of Danvers, Mass. This imaging system is the subject of U.S. Pat. No. 7,397,895, issued on Jul. 8, 2008 to Bailey et al. The scanning system is illustrated in FIG. 1.

FIG. 1 shows the scanning system of NeuroLogic Corp. This scanning system 1 includes a frame 2, and a CT imaging unit 4 mounted to the frame 2. The CT imaging unit 4 is adapted to scan anatomical objects and generate images of such anatomical objects, such as the head of the patient. A transport mechanism 6 is mounted to the frame. The transport mechanism 6 allows fine movement for moving the CT imaging unit 4 precisely relative to the patient during scanning. The imaging system 1 can further include an on-board networking unit mounted to connect the CT imaging unit to a workstation, the hospital's Picture Archiving and Communication (PAC) system, or other Information Technology (IT) network without requiring the use of conventional physical cabling. There is also an on-board power unit mounted to the frame. The onboard power unit is adapted to provide the electrical power needed to operate the CT imaging unit 4, the transport mechanism 6 and the networking unit.

In FIG. 1, it can be seen that the frame 2 includes a pair of arcuate frame members 8 and 9. These arcuate members 8 and 9 are rigidly connected to the imaging unit 4 and provide a surface that facilitates the ability to physically move the imaging system 1. As such, the arcuate frame elements 8 and 9 can provide a strong surplus for securement external objects, as will be described hereinafter.

FIGS. 2 and 3 show prior art mobile emergency medical vehicles that are currently manufactured by Frazer, Inc. of Houston, Tex. Each of these mobile emergency medical vehicles 10 is the subject of U.S. Pat. No. 4,672,296 (issued on Jun. 9, 1987) and U.S. Pat. No. 4,785,227 (issued on Nov. 15, 1988) to J. Griffin. In particular, each of the mobile emergency medical vehicles shown in FIGS. 2 and 3 are unique in that it incorporates a generator 14 that is mounted on a skid-type mounting frame 13 and fitted within the compartment 12 of the mobile emergency medical vehicle 10. The mobile emergency medical vehicle 10 is built on a conventional truck chassis having the main transport engine located beneath the hood in a manner well known in the art.

The patient compartment 11 is mounted on the rearward portion of the truck chassis in a manner also known in the prior art. The mobile emergency medical vehicle 10 of these prior art patents has the vehicle essentially self-supported with regard to its electrical requirements. The auxiliary engine and generator are mounted exteriorly of the patient module so that the exhaust system extends outwardly so as to deliver minimal noise and vibration to the patient module. The electrical output of the generator 14 is preferably capable of providing 4 to 6 kW of continuous electrical power and is capable of continuously delivering 115 volts of AC power to the electrical load center of the patient compartment 11. The load center provides distribution of the primary output of the generator 14 to air-conditioning and heating. As such, the generator 14 provides the power necessary to supply both cooling and heating to the patient compartment. The generator which is preferably located on the passenger side at a rear lower corner of the vehicle provides module power for emergency lights, air conditioning, heating, suction, interior lights, and the like.

Prior to the development of the mobile emergency medical vehicle of Frazier, Inc., all of the power requirements for ambulances were achieved through the use of an alternator directly connected to the engine. As such, the power to the patient compartment had to be supplied from energy stored in the battery or directly by the alternator. Typically, during procedures, the engine would remain idling so as to continuously supply power. Unfortunately, the power supplied by an alternator is relatively a poor quality of power. There are substantial fluctuations in the power levels provided by such alternators. Under other circumstances, the emergency vehicle would enter a closed area. As such, there would always remain the danger of carbon monoxide poisoning in those events in which the engine is maintained in an idling mode for the purposes of supplying power.

In the past, a variety of patents have issued relating to scanning systems for mobile emergency vehicles. For example, U.S. Pat. No. 4,181,347, issued on Jan. 1, 1980 to R. G. Clark, shows a mobile computerized tomography unit that includes a vehicle trailer, a CT scanner gantry and patient table, a means for mounting the CT-scanner gantry, and a mini-computer system for the display and data processing of the CT scanner mounted in the trailer. Shock-absorbing components are provided so as to insulate the CT scanner from undue shocks.

U.S. Pat. No. 4,449,746, issued on May 22, 1984 also to R. G. Clark, shows another mobile computerized tomography unit. This system also includes a trailer with a tomography system built therein.

U.S. Pat. No. 5,097,497, issued on Mar. 17, 1992 to Deucher et al., provides a deployable CT medical system. The CT medical system has a gantry that is mounted by helical wire rope shock isolators to the floor of a shelter at about a 60° angle relative to a central axis of the shelter. Mechanical assemblies limit movement of the tiltable gantry portion relative to fixed gantry portions. A CT scanner control console is mounted adjacent an opposite end of the shelter on a shock isolator.

U.S. Pat. No. 6,481,887, issued on Nov. 19, 2002 to P. J. Mirabella, shows a mobile medical image scanner and a teleradiology system that are incorporated into an ambulance or other vehicle to permit the patient be diagnosed while en route for a treatment facility, such as a trauma center. The system obtains medical image data while the patient is been transported in the vehicle and transmits the medical image data to a receiver in a location which is remote from the vehicle. At the remote location, the transmitted medical image data is displayed in a humanly discernible manner and interpreted by qualified physician who then communicates diagnostic information to the technicians in the vehicle and/or to the treating physicians at the treatment facility.

U.S. Pat. No. 6,625,252, issued on Sep. 23, 2003 also to P. J. Mirabella, describes a mobile medical image scanner and teleradiology system is incorporated into an ambulance or other vehicle so as to permit the patient to be diagnosed. The system obtains medical image data during the transport of the patient in the vehicle. The system will transmit medical image data to a receiver at a hospital or other location. This data can then be remotely interpreted.

Unfortunately in these prior art systems, there is no convenient way of putting a CT scanner within the vehicle. Additionally, given the need for maneuverability and speed in the emergency vehicle, it was very difficult to properly mount the CT scanner so that it would not be affected adversely by shocks. Additionally, and furthermore, it is difficult to install the CT scanner in a manner in which the patient can be properly placed into proximity to the CT scanner.

It is an object of the present invention to provide an emergency medical vehicle having a CT scanner therein.

It is another object of the present invention provide an emergency medical vehicle in which the CT scanner can be fixed to the wall of the vehicle during movement of the vehicle and deployed from the wall once the vehicle reaches the desired destination.

It is another object of the present invention to provide an emergency vehicle which can serve to effectively diagnose different types of strokes, to facilitate treatment for such strokes, and save lives as a result of such treatment.

It is another object of the present invention provide an emergency medical vehicle having a CT scanner therein which avoids excess exposure to radiation by operators of the CT scanner.

It is another object of the present invention to provide an emergency medical vehicle which can maintain the stretcher or cot in an elevated fixed position.

It is another object of the present invention to provide an emergency medical vehicle having a CT scanner therein in which the stability of the emergency medical vehicle is enhanced.

It is another object of the present invention to provide an emergency medical vehicle that provides clean and sufficient power to the CT scanner.

It is another object of the present invention to provide an emergency medical vehicle which avoids the need for idling the vehicle during the supply of power to the patient compartment.

It is still a further object of the present invention to provide an emergency medical vehicle that has sufficient power to supply both the air-conditioning system and the CT scanner.

It is still further object of the present invention to provide an emergency medical vehicle which improves the ability to maintain the integrity of the CT scanner during travel and use.

These and other objects and advantages of the present invention will become apparent from a reading of the attached specification and appended claims.

BRIEF SUMMARY OF THE INVENTION

The present invention is an apparatus that comprises a vehicle having a patient compartment and a motor, a generator cooperative with the patient compartment, and a CT scanner positioned in the patient compartment and connected to the generator so as to supply power to the CT scanner. The patient compartment has a front wall, a floor and a pair of side walls. The CT scanner is releasably affixed to the front wall of the patient compartment. In the present invention, the generator is operable independently of the motor of the vehicle.

The front wall of the patient compartment has at least one receptacle affixed thereto. The CT scanner has at least one pin connector extending toward the front wall. The pin connector is releasably received by the receptacle. In particular, the receptacle comprises a first pair of receptacles positioned at a first elevation and a second pair of receptacles positioned at a second elevation. The first elevation is higher than the second elevation. The pin connector includes a first pair of pin connectors and a second pair of pin connectors that are respectively receivable in the first and second pairs of receptacles. The CT scanner has a frame extending therefrom. The pin connector is affixed to the frame of the CT scanner. The receptacle includes a quick-release lock thereon. This quick-release lock is movable between a release position and a locked position. The locked position is adapted to lock the pin connector within the receptacle.

The patient compartment has a door on one of the pair of side walls. A shelf is mounted on the door so as to be extendable in an orientation transverse to the door.

At least one chock is affixed to the floor of the patient compartment. This chock is adapted to receive a wheel of a stretcher therein. The stretcher is removably positioned in the patient compartment. The stretcher is positioned rearwardly of the CT scanner. The stretcher has a plurality of wheels connected thereto. At least one of the pair of side walls of the patient compartment has a strap-receiving element thereon. The present invention further includes a strap that is releasably fastened to the stretcher and attached to the strap-receiving element. The strap is adapted to fix a position of the stretcher within the passenger compartment. A headboard is positioned on the stretcher so as to extend toward the CT scanner.

This foregoing section is intended to describe, with particularity, the preferred embodiments of the present invention. It is understood that modifications to this preferred embodiment can be made within the scope of the present invention. As such, this section should not be construed, in any way, as limiting of the broad scope of the present invention. The present invention should only be limited by the following claims and their legal equivalents.

DETAILED DESCRIPTION OF THE INVENTION

Figure 3:
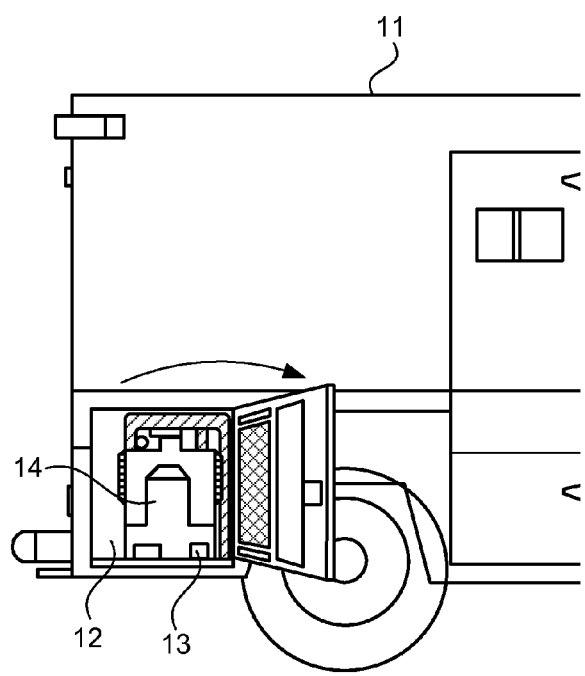
FIG. 3 is a side view of the emergency medical vehicle of the prior art showing, in particular, the generator located within a compartment below the patient compartment.
Figure 4:
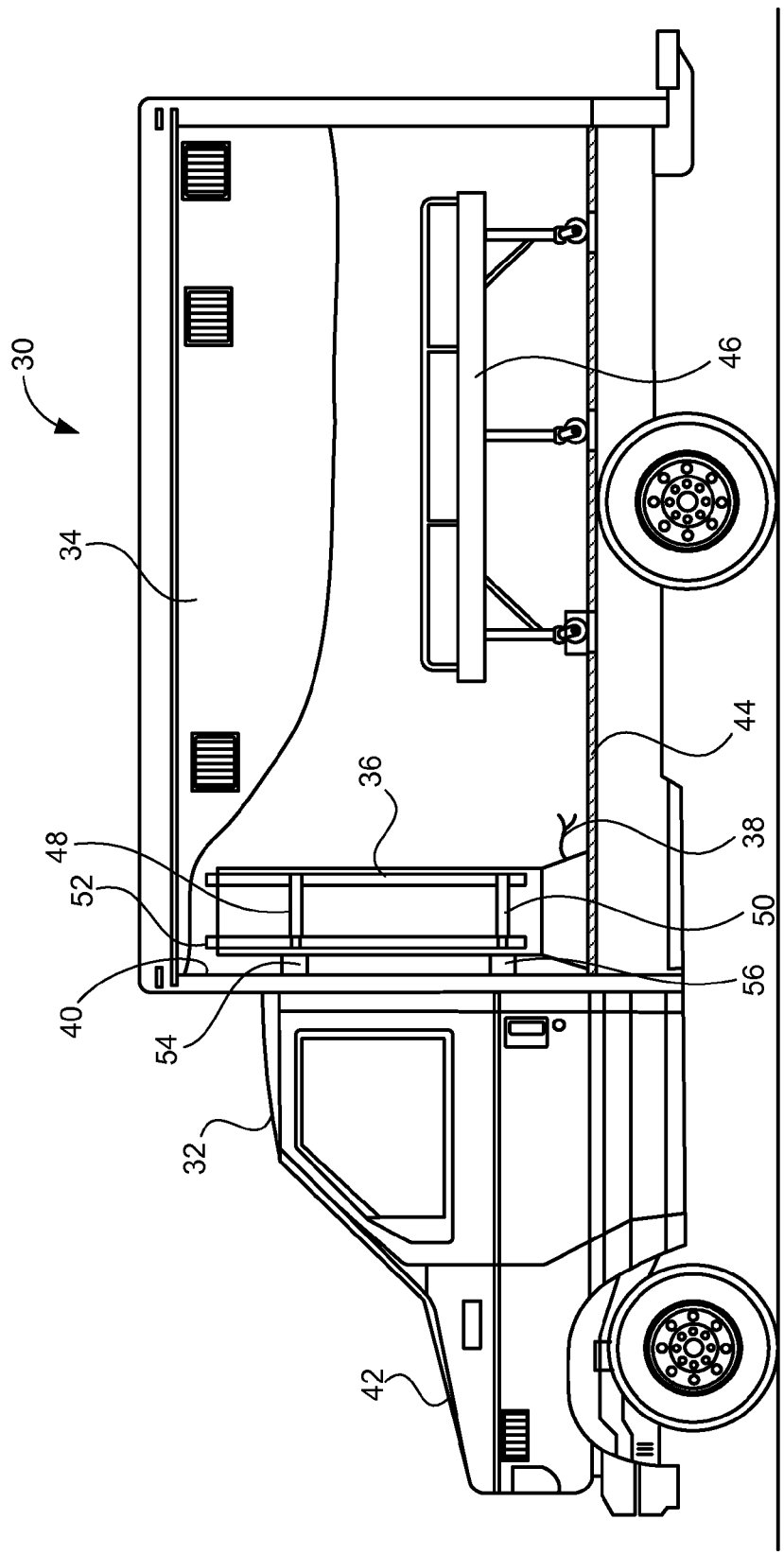
FIG. 4 is a is a partially cutaway side elevational view of the emergency medical vehicle of the present invention showing the CT scanner as located in a fixed position.

Referring to FIG. 4, there shown the apparatus 30 of the present invention. The apparatus 30 includes a vehicle 32 that includes a patient compartment 34, a generator (shown in FIGS. 2 and 3), and a CT scanner 36 positioned in the patient compartment 34. The CT scanner 36 is connected by a line 38 to the generator such that the generator can supply power to the CT scanner 36. In FIG. 4, the CT scanner 36 is shown as rigidly affixed to the front wall 40 of the patient compartment 34 of the vehicle 32.

Figure 1:
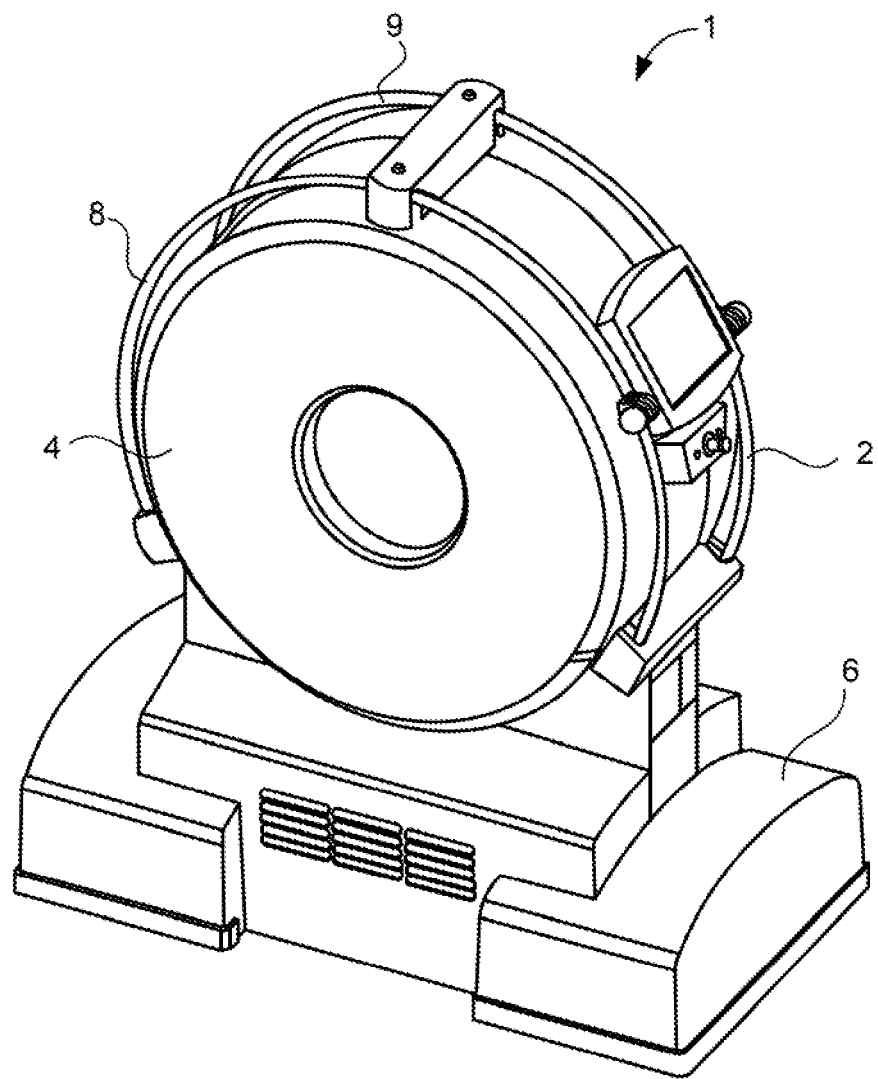
FIG. 1 is a perspective view of a prior art CT scanner.
Figure 2:
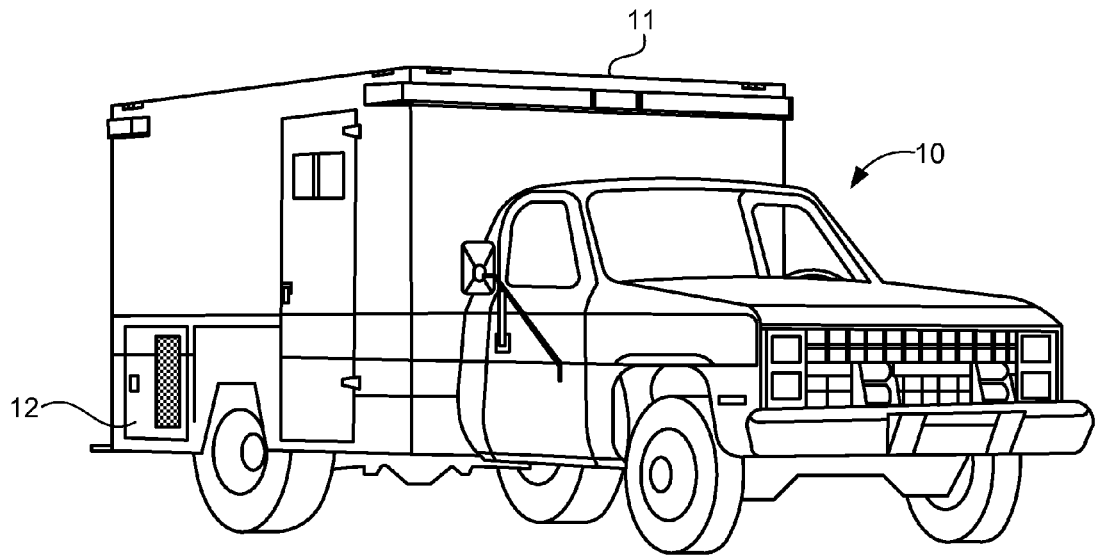
FIG. 2 is a frontal perspective view of prior art emergency medical vehicle as used in the present invention.

In FIG. 4, the vehicle 32 has a configuration similar to the mobile emergency medical vehicle of Frazer, Inc., as shown in FIGS. 2 and 3 herein before. As was stated hereinbefore, the vehicle 32 will include a generator located toward the rear of the patient compartment 34. The generator can operate independently of the motor of the vehicle so as to directly supply power to air-conditioning systems located within the patient compartment 34 and to supply power to the CT scanner 36. The motor of the vehicle 32 will be positioned under the hood 42 at the front of the vehicle 32.

In FIG. 4, it can be seen that the patient compartment 36 includes a floor 44. Floor 44 is positioned so as to allow the stretcher 46 to be placed thereon. The stretcher 46 is spaced at a distance away from the mounted CT scanner 36. As will be described hereinafter, the stretcher 46 is illustrated in an upwardly extending position. In the prior art emergency medical vehicle of FIGS. 2 and 3, the stretcher 46 would have to be in a lowered condition so as to allow the latching mechanisms on the floor 44 to properly engage with the frame of the stretcher 46 so as to lock the position of the stretcher 46 in its lowered positioned within the patient compartment 34. In the present invention, the stretcher 46 is maintained in an elevated position above the floor 44 so that the head of the patient located on the stretcher 46 can be placed in proximity to the opening of the CT scanner 36.

The CT scanner 36 includes a pin connector 48 and a pin connector 50. The pin connector 48 is secured to the arcuate frame member 52 of the CT scanner 36. The pin connector 50 is also secured to the arcuate frame member 52 of the CT scanner 36. A receptacle 54 is affixed to the inner surface of the front wall 40 of the patient compartment 34. Another receptacle 56 is also mounted to the front wall 40 of the patient compartment 34. The receptacle 54 (along with the pin connector 48) is located at a higher elevation than the receptacle 56 and the pin connector 50. These different elevations of pin connectors and receptacles serves to assure stability of the connection between the CT scanner 36 and the front wall 40. If the receptacles 54 and 56 were located at the same elevation, then there could be flexing of the CT scanner 36 during the travel of the vehicle 32. This flexing would occur horizontally during travel. As will be described hereinafter, there is a first pair of pin connectors and a second pair pin connectors, along with a pair of first pair of receptacles and a second pair of receptacles.

With reference to FIG. 4, the CT scanner 36 is illustrated in its proper position during travel of the vehicle 32. The CT scanner 36 is rigidly mounted to the front wall 40 so as to generally isolate the CT scanner 36 against vibration. Additionally, the location of the CT scanner 36 at a location adjacent to the front wall 40 will place the relatively heavy CT scanner 36 directly above a center-of-gravity of the vehicle 32. As such, this greatly enhances the stability of the vehicle 32 during travel and turning.

Figure 5:
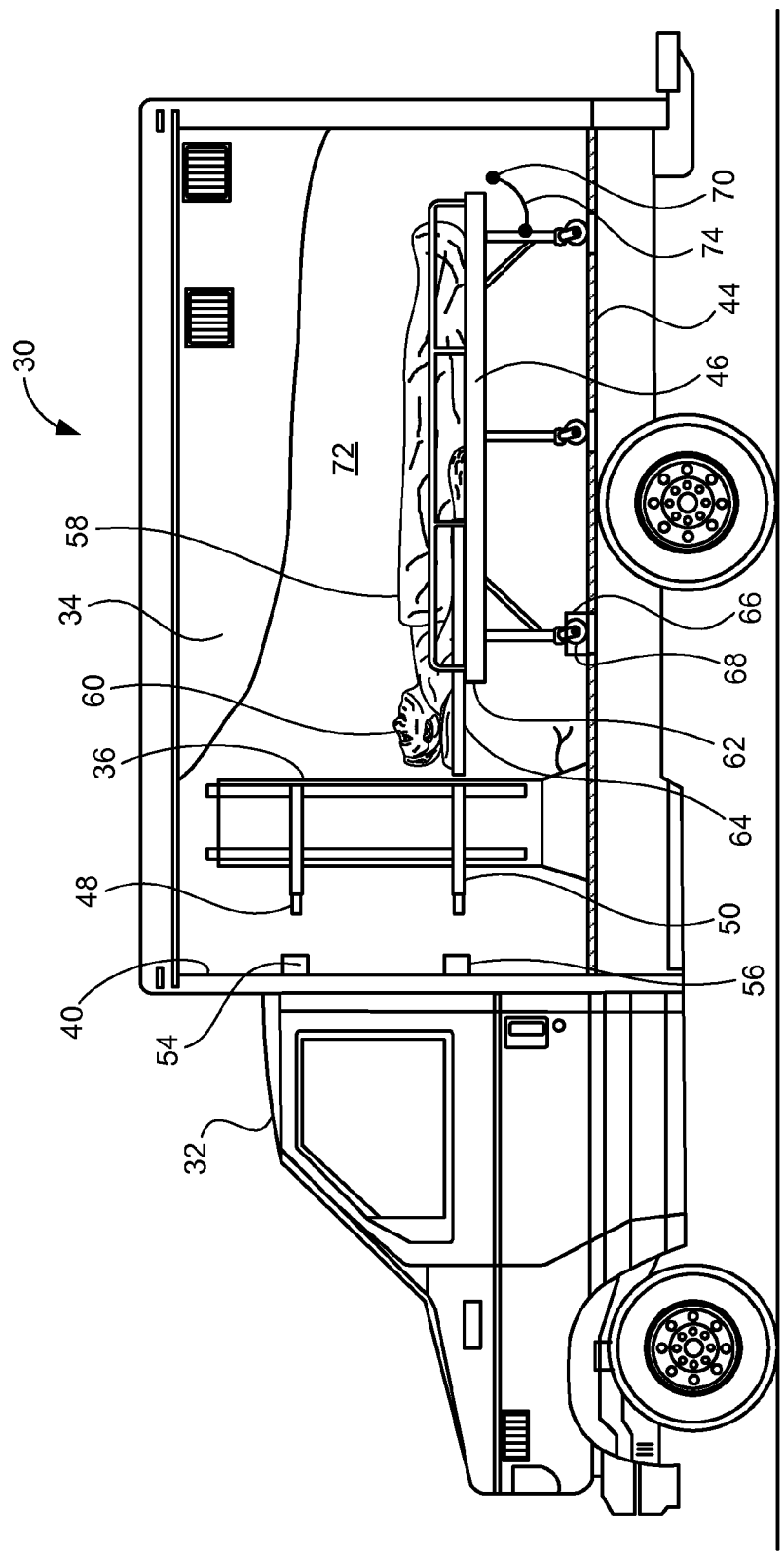
FIG. 5 is a partially cutaway side elevational view of the emergency medical vehicle of the present invention showing the CT scanner in a position during use.

FIG. 5 shows the apparatus 30 of the present invention in which the CT scanner 36 has been separated from the front wall 40 of the passenger compartment 34 so as to be in a proper position for use. A patient 58 is illustrated as positioned on the stretcher 46. It can be seen that the head 60 of the patient 58 is maintained in an elevated position as a result of the elevated positioning of the stretcher 46. Additionally, for the proper operation of the CT scanner 36, it will be necessary for the head 60 of the patient 58 to extend forwardly of the front end 62 of the stretcher 46. As a result, the present invention incorporates a headboard 64 located below the head 60 of the patient 58. The headboard 64 is maintained in a generally horizontal orientation by the force exerted by the back of the patient 58 against the top surface of the headboard 64. As a result, the head 60 can be properly supported beyond the front end 62 of the stretcher 46.

In order to enhance stability of the stretcher 46 in its elevated position, a chock 66 is affixed to the floor 44 of the passenger compartment 34. The chock 66 serves to receive the wheel 68 of the stretcher 46 therein. Chock 66 is illustrated in FIG. 5 in a transparent fashion so as to illustrate the manner in which the wheel 68 is received therein. The chock 66 serves to prevent any further forward movement of the stretcher 46 and the wheel 68.

A strap-receiving element 70 can be mounted to a wall 72 of the passenger compartment 34. The strap-receiving element 70, as will be described hereinafter, can be in the nature of a D-ring that is secured to the wall 72. Various other appliances can be provided so as to act as a technique for receiving the strap 74. The strap 74 can be secured to a leg of the stretcher 46 or secured to the body of the stretcher 46. The strap 74 is mounted to the strap-receiving element 70 so as to exert a strong force therewith so as to properly stabilize the elevated stretcher 46 in its desired position within the passenger compartment 34.

The CT scanner 36 is shown as removed from the receptacles 54 and 56. In particular, the pin connector 48 has been released from the receptacle 54. Similarly, the pin connector 50 has been released from the receptacle 56. As will be described hereinafter, each of the connectors 54 and 56 includes a quick-release lock so that a minor manipulation of the lock can allow for the release of the pin connectors 48 and 50.

The CT scanner 36 is moved from its position adjacent to the front wall 40 and positioned adjacent to the head 60 of the patient 58. As such, the generator can supply power to the CT scanner 36 so as to allow for the desired operation of the CT scanner. The results of the CT scan are available through known technology. As a result, the paramedics or technicians associated with the apparatus 30 can quickly evaluate the type of stroke suffered by the patient 58.

It should be noted in the present invention that a great deal of power is required for the operation of the CT scanner 36, along with the air-conditioning systems of the vehicle 32. Conventional alternators associated with the motor of the vehicle 32 would not be sufficient for supplying the power requirements of both the CT scanner 36 and the air-conditioning equipment. In the present invention, since the generator is independent of the motor, the generator can be sized approximately 7 kW so as to supply the requisite power to both systems. As such, the integrity of the CT scanner 36 is preserved by being maintained in a proper temperature environment. If the CT scanner 36 were exposed to extreme temperatures, then it could become damaged. Additionally, the present invention allows the motor of the vehicle 32 to be turned off during the procedure. This will serve to reduce vibrations that can occur as a result of the idling of the motor. This causes a more accurate scan to be achieved. Furthermore, the generator is known to provide clean power and proper power factors. As a result, through the use of the generator of the vehicle 32, a clean and conditioned power can be supplied to the CT scanner 36. Once again, this enhances the integrity of the CT scanner 36 and improves the scanning results.

Following the CT scan of the patient 36, the CT scanner 36 can be placed back against the front wall such that the pin connectors 48 and 50 properly engage with the receptacles 54 and 56. As a result, the vehicle 32 is now ready for delivery of the patient 58 to a hospital or other treatment facility. The stretcher 46 can also be lowered and locked to the floor 44 of the patient compartment 34 during such travel. This will maintain both the CT scanner 36 and the patient 58 in a safe condition during travel.

Figure 6:
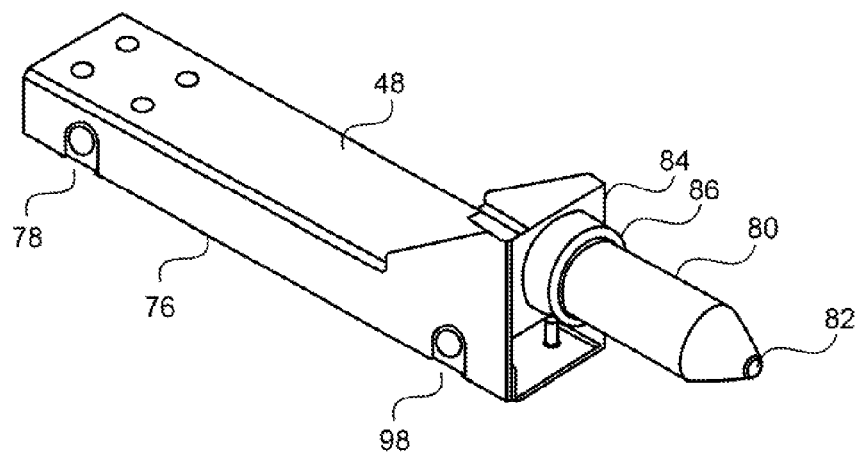
FIG. 6 is a perspective view showing the pin connector as used in the present invention.

FIG. 6 shows the pin connector 48. Each of the pin connectors associated with the CT scanner 36 of the present invention will have a similar configuration. The pin connector 48 includes a body 76 that includes an aperture 78 adjacent the rearward end thereof. Aperture 78 will be suitable for receiving the frame member of the CT scanner therein. A pin 80 projects forwardly of the body 76. The pin 80 has a pointed end 82 that can easily guide into the receptacle. A bracket 84 extends upwardly from the body 76 so as to secure the rear end of the pin 80 thereto. Bracket 84 has a generally U-shaped configuration and is affixed by fasteners to the body 76. The pin 80 includes a shoulder 86 adjacent to the bracket 84. Shoulder 86 provides an abutment surface against the receptacle.

Figure 7:
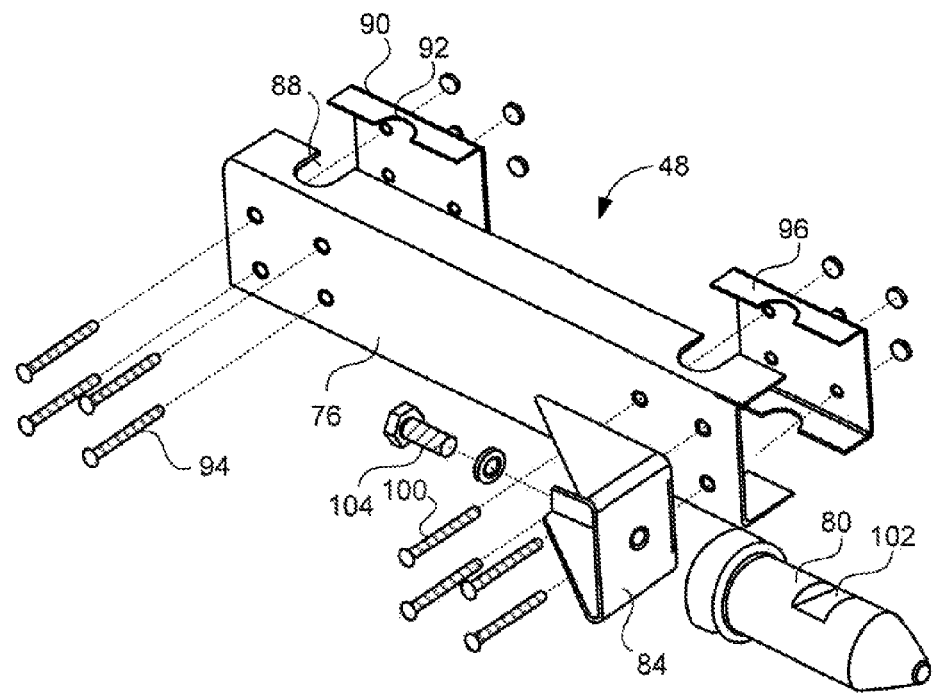
FIG. 7 is a perspective exploded view of the pin connector of the present invention.

FIG. 7 is an exploded view of the pin connector 48. The body 76 has a U-shaped slot 88 formed adjacent the rearward end thereof. The U-shaped slot 88 serves to define a portion of the aperture 78. Another bracket 90 also includes a U-shaped slot 92 that faces the U-shaped slot 88 of the body 76. During installation, the U-shaped slot 88 can be placed over the arcuate frame member 52 of the CT scanner 36. The U-shaped slot 92 can then be placed on an opposite side of the arcuate frame member 52 of the CT scanner 36. When the bracket 90 is joined to the body 76 through the use of fasteners 94, the U-shaped slot 88 and the U-shaped slot 92 will define the aperture 78 and rigidly secure the body 76 to the arcuate frame member 52. A similar construction is located at the forward end of the body 76. A further bracket 96 can be mounted to correspond with the forward end of the body 76. This also defines an aperture 98 which can receive the other arcuate frame member 52 of the CT scanner 36. Fasteners 100 will serve to secure the further bracket 96 to the forward end of the body 76 so as to lock over the arcuate frame member 52 of the CT scanner 36. The bracket 84 is illustrated as also attached by fasteners 100 to the body 76 into the brackets 96. The pin 80 is shown as having a milled notch 102 formed across a chord of the circumference of the pin 80. This notch 102 is suitable for engaging with the quick-release lock of the receptacle. A bolt 104 can be fastened to the pin 80 so as to rigidly affixed the pin 80 against the bracket 84.

Figure 8:
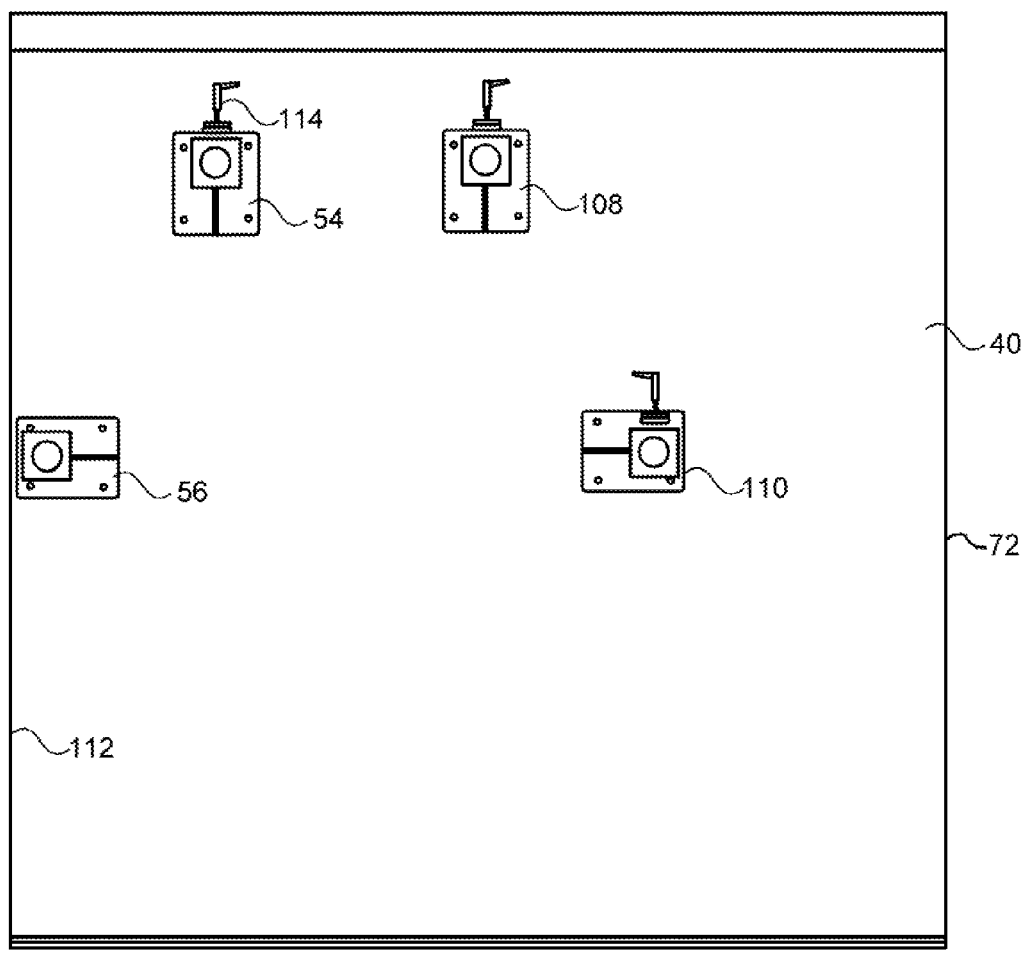
FIG. 8 is a view of the receptacles as positioned on the front wall of the patient compartment of the emergency medical vehicle of the present invention.

FIG. 8 shows the orientation of the various receptacles 54, 56, 108 and 110 on the front wall 40 of the patient compartment 34. In particular, can be seen that the receptacle 54 is at an elevation greater than the receptacle 56. Receptacle 108 is at the same elevation as receptacle 54 but spaced horizontally away from receptacle 54. Similarly, the receptacle 110 is at the same elevation as the receptacle 56 but spaced from the receptacle 56. The receptacle 56 is adjacent to a side wall 112 of the vehicle. The orientation of the receptacles 54 and 108 serves to prevent deflection of the CT scanner horizontally. The different elevations between the receptacle 54 and 56, along with the different elevations of the receptacles 108 and 110 serves to prevent horizontal deflections of the CT scanner 36. This configuration facilitates the stability of the CT scanner during travel and serves to minimize the effect of vibrations on the CT scanner during the movement of the emergency vehicle. It can be seen in FIG. 8 that each of the receptacles 54, 108 at 110 includes a quick-release lock 114.

Figure 9:
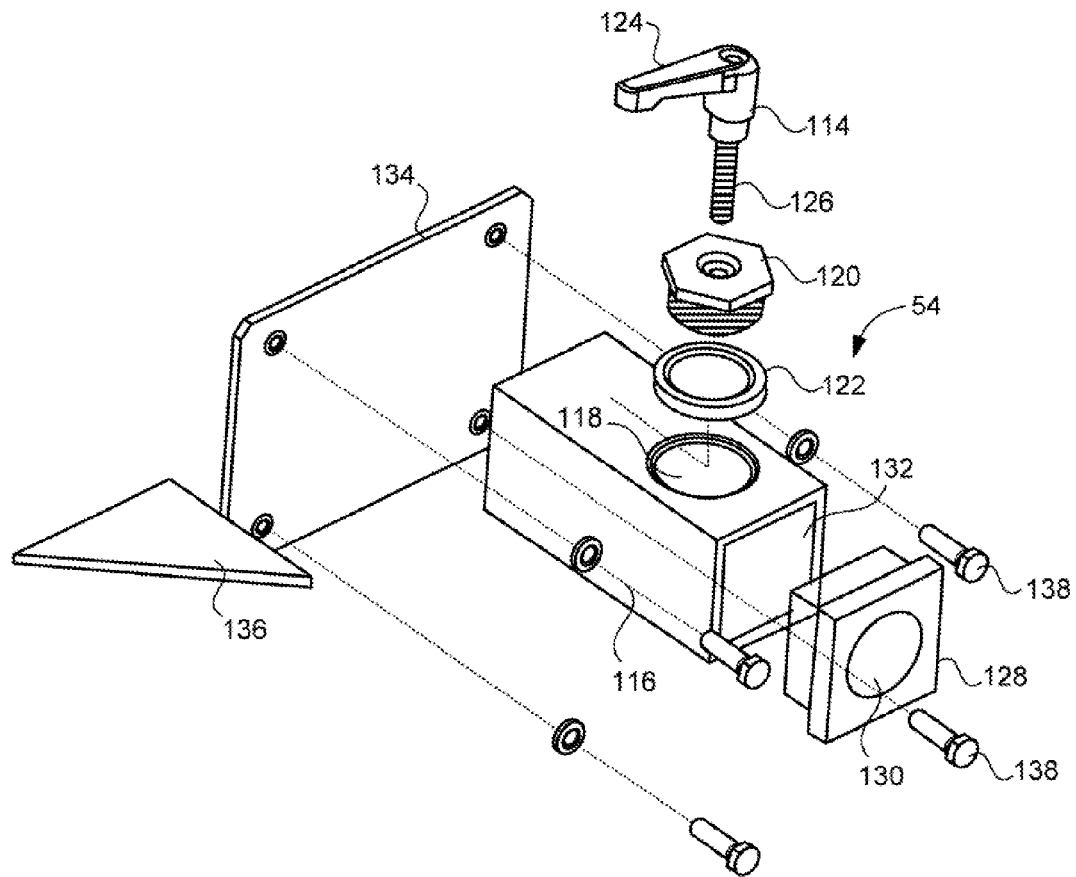
FIG. 9 is a perspective exploded view of the receptacle as used on the front wall of the emergency medical vehicle of the present invention.

FIG. 9 is an exploded view of the receptacle 54. Receptacles 108 and 110 will have a similar configuration to receptacle 54. Receptacle 56 has the quick-release lock 114 removed therefrom. Receptacle 54 includes a square tubular body 116 having an opening 118 on the top thereof. A hex head 120 is mounted to an aluminum coupling 122 at the opening 118. The quick-release lock 114 includes a handle 124 extending transversely outwardly thereof. A shank 126 of the quick-release lock 114 will extend downwardly into the interior of the square tubular body 116. A bushing 128 includes the pin-receiving hole 130 at the forward end thereof. The bushing 128 is in the nature is formed of a Nylatron™ material. The bushing 128 is fitted into the open end 132 of the square tubular body 116. The square tubular body 116 can be connected to a panel 134. A gusset 136 can be affixed to the panel 134 and to the square tubular body 116 so as to secure the square tubular body. Suitable fasteners 138 are provided so as to fasten the panel 134 to the front wall 40 of the vehicle.

When the pin is inserted into the hole 130, the handle 124 can be rotated for one quarter rotation so as to lock the pin in position within the square tubular body 116. The reverse turning of the handle 124 and the quick-release lock 140 can serve to release the pin from its locked configuration. The use of the bushing 128 further facilitates insulation of the CT scanner against shocks and vibrations. The outer end of the bushing 128 will generally bear against the shoulder 86 of the pin 80. This configuration has been found to enhance resistance against vibration and shock absorption in a superior manner to other techniques.

Figure 10:
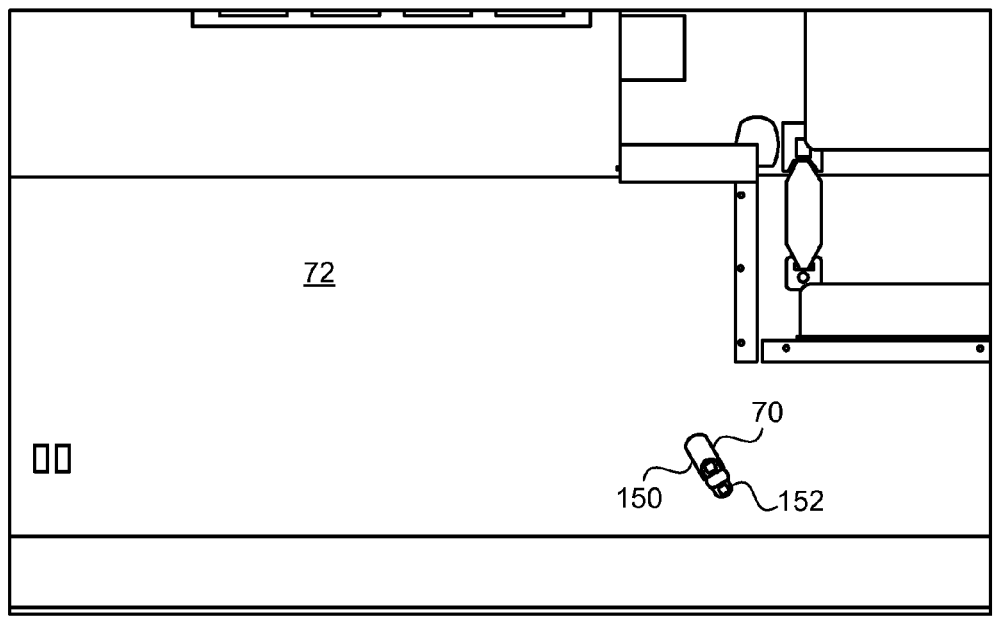
FIG. 10 is a side elevational view showing the strap-receiving element as attached to a side wall of the emergency medical vehicle of the present invention.

FIG. 10 illustrates the side wall 72 of the vehicle. In FIG. 10, the strap-receiving element 70 can be seen. The strap-receiving element 70 is in the nature of a D-ring 150 that can be anchored by bracket 152 to the side wall 72. The D-ring 150 can serve to rigidly secure a strap 74 thereto. This facilitates the ability to fix a position of the stretcher 46 in an elevated position within the interior of the patient compartment 34.

Figure 11:
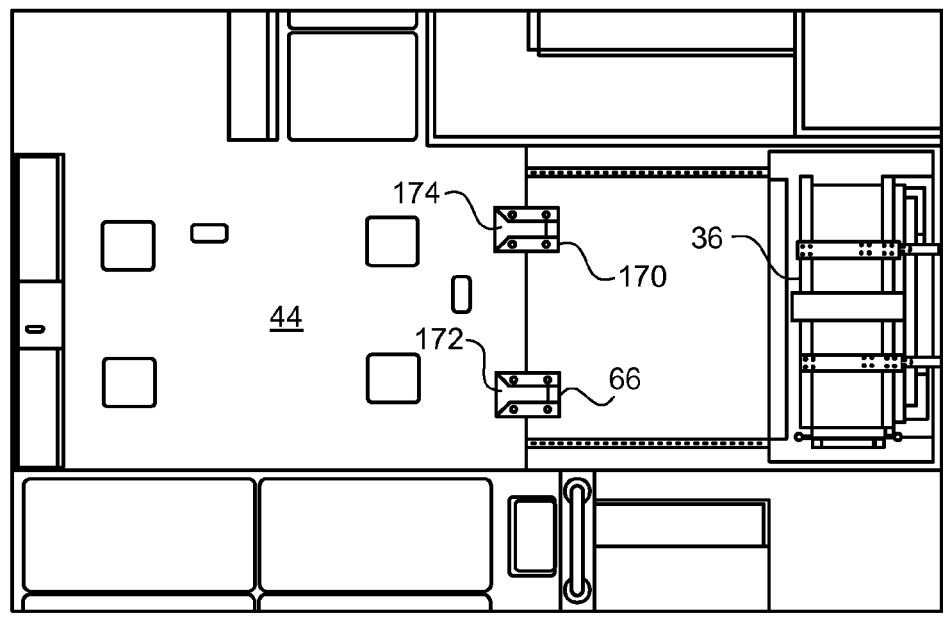
FIG. 11 is a plan view showing the placement of chocks on the floor of the emergency medical vehicle of the present invention.

FIG. 11 shows the floor 44 of the passenger compartment 34. In particular, there is shown a first chock 66 and a second chock 170 that are affixed in spaced relationship to each other and to the floor 44. The chock 66 includes a slot 172 which opens at a rear of the chock 66. The chock 170 also includes a slot 174 that opens at a rear of the chock 170. Each of the slots 172 and 174 includes a funnel-type opening so as to facilitate the ability to funnel the wheels 68 of the stretcher 46 into each of the slots 172 and 174. Each of the chocks 66 and 170 is located rearwardly and in spaced relationship to the CT scanner 36. In normal use, the forward wheels 68 of the stretcher 46 will move into each of the slots 172 and 174 of the chocks 66 and 170. As such, the chocks 66 and 170 will serve to fix the position of the wheels 68 and to prevent further forward movement.

Figure 12:
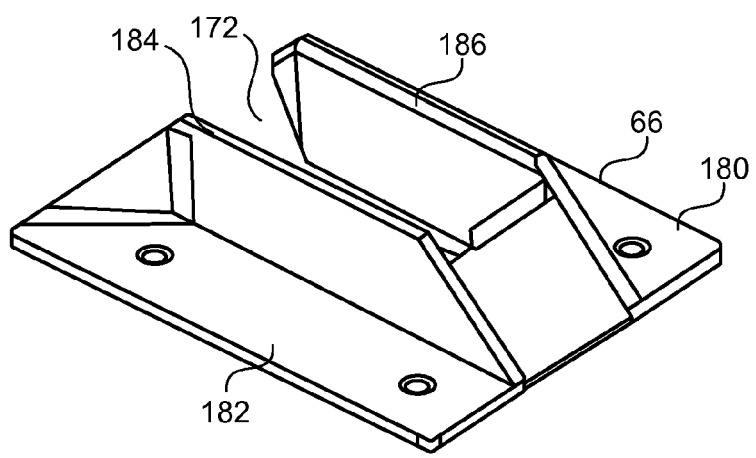
FIG. 12 is a perspective view of a single chock as used in the present invention.

FIG. 12 is a perspective view of the chock 66. The chock 66 includes a pair of flanges 180 and 182 that extend outwardly of raised sides 184 and 186. The raised sides 184 and 186 serve to define the slot 172. The raised sides 184 and 186 will serve to prevent the wheels of the stretcher from pivoting. The flanges 180 and 182 can be secured to the floor 44 through the use of appropriate fasteners.

Figure 13:
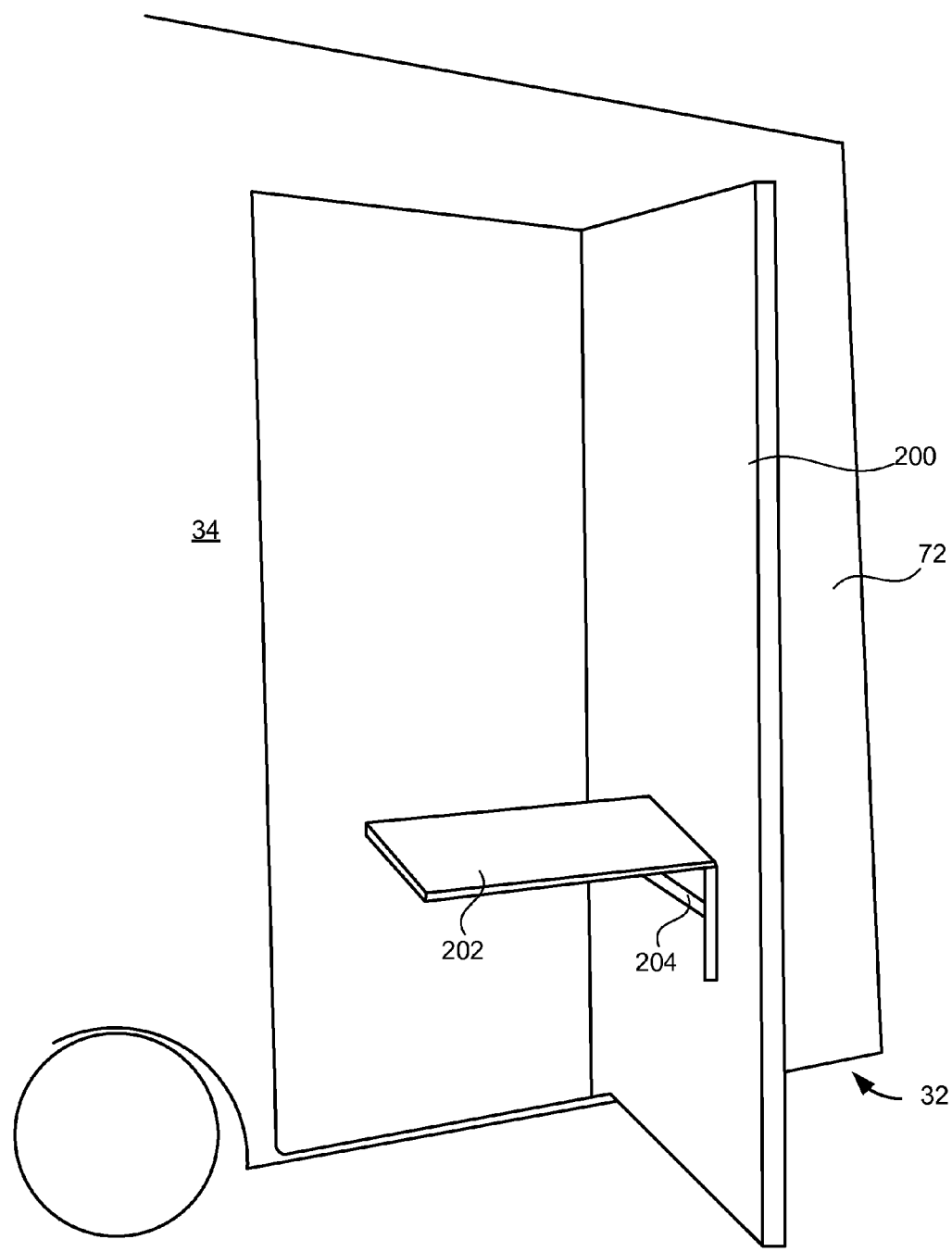
FIG. 13 is a perspective view showing the door and shelf of the emergency medical vehicle of the present invention.

FIG. 13 is an illustration of a unique feature to the present invention. In particular, the side wall 72 of the vehicle 32 is shown. A door 200 is hingedly mounted to the side wall 72 so as to allow entrance into an interior of the patient compartment 34. Importantly, it can be seen that there is a shelf 202 that extends generally transversely outwardly of the door 200. A slide mechanism 204 allows the shelf 202 to move between a position bearing against the door 200 and the position shown in FIG. 13. The shelf 202 is particularly configured so as to receive the various control instruments, computers, displays and other items thereon. As such, during the operation of the CT scanner the technician can operate and monitor the CT scanner from a location outside of the patient compartment 34. This serves to minimize exposure of the worker to the radiation of the CT scanner. It assures that the technician is positioned a sufficient distance from the CT scanner so as to avoid any adverse health effects therefrom. After the CT scan is carried out, the shelf 202 can be lowered and locked in positioned for further travel.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. An apparatus comprising:
 a vehicle having a patient compartment and a motor therein, said patient compartment having a front wall and a floor and a pair of side walls;
 a generator cooperative with said patient compartment; and
 a Computerized Tomography (CT) scanner positioned in said patient compartment and connected to said generator so as to supply power to said CT scanner, said CT scanner being releasably affixed to said front wall of said patient compartment, said front wall of said patient compartment having at least one receptacle affixed thereto, said CT scanner having at least one pin connector extending toward said front wall, the pin connector being releasably received by the receptacle, said at least one receptacle comprising a first pair of receptacles positioned at a first elevation and a second pair of receptacles positioned at a second elevation, said first elevation being higher than said second elevation, said at least one pin connector comprising first pair of pin connectors and a second pair of pin connectors respectively receivable in said first and second pairs of receptacles.

2. The apparatus of claim 1, said generator being operable independently of said motor of said vehicle.

3. The apparatus of claim 1, said CT scanner having a frame extending therefrom, said at least one pin connector being affixed to said frame of said CT scanner.

4. The apparatus of claim 1, said at least one receptacle having a quick-release lock thereon, said quick-release lock being movable between a release position and a locked position, said locked position adapted to lock the pin connector within the receptacle.

5. The apparatus of claim 1, further comprising:
at least one chock affixed to said floor of said patient compartment, said chock adapted to receive a wheel of a stretcher therein.

6. The apparatus of claim 1, further comprising:
a stretcher removably positioned in said patient compartment, said stretcher positioned rearwardly of said CT scanner, said stretcher having a plurality of wheels connected thereto.

7. The apparatus of claim 6, further comprising:
a headboard positioned on said stretcher and extending toward said CT scanner.

8. The apparatus of claim 6, further comprising:
a chock affixed to said floor of said patient compartment, said chock receiving the wheel of said stretcher therein.

9. The apparatus of claim 7, at least one of said pair of side walls of said patient compartment having a strap-receiving element thereon, the apparatus further comprising:
a strap being releasably fastened to said stretcher and attached to said strap-receiving element, said strap adapted to fix a position of said stretcher within said passenger compartment.

10. An apparatus comprising:
a vehicle having a patient compartment and a motor therein, said patient compartment having a front wall and a floor and a pair of side walls;
a power supply cooperative with said patient compartment; and
a Computerized Tomography (CT) scanner positioned in said patient compartment and connected to said power supply so as to supply power to said CT scanner, said CT scanner being movable between a first position and a second position, said first position being rigidly affixed to said front wall of said patient compartment, said second position being spaced from said front wall, said front wall of said patient compartment having at least one receptacle affixed thereto, said CT scanner having at least one pin connector extending toward said front wall, the pin connector being fixedly received by the receptacle when said CT scanner is in said first position, said at least one receptacle comprising a first pair of receptacles positioned at a first elevation and a second pair of receptacles positioned at a second elevation, said first elevation being higher than said second elevation, said at least one pin connector comprising a first pair of pin connectors and a second pair of pin connectors respectively receivable in said first and second pairs of receptacles.

11. The apparatus of claim 10, said power supply being a generator that is operable independently of said motor.

12. The apparatus of claim 10, further comprising:
a stretcher positioned in said patient compartment, said CT scanner being adjacent to one end of said stretcher when in said second position.

13. The apparatus of claim 12, said stretcher being removably positioned in said patient compartment, said stretcher having a plurality of wheels connected thereto, the apparatus further comprising:
a chock affixed to said floor of said patient compartment, said chock receiving the wheel of said stretcher therein; and
a strap being releasably fastened to said stretcher and attached to one of said pair of side walls, said strap adapted to fix a position of said stretcher within said passenger compartment.

14. The apparatus of claim 12, further comprising:
a headboard positioned on said stretcher and extending toward said CT scanner.

15. An apparatus comprising:
a vehicle having a patient compartment and a motor therein, said patient compartment having a front wall and a floor and a pair of side walls;
a generator cooperative with said patient compartment; and
a Computerized Tomography (CT) scanner positioned in said patient compartment and connected to said generator so as to supply power to said CT scanner, said CT scanner being releasably affixed to said front wall of said patient compartment, said patient compartment having a door on one of said pair of side walls, the apparatus further comprising:
a shelf mounted on said door so as to be extendable in an orientation generally transverse to said door.

16. An apparatus comprising:
a vehicle having a patient compartment and a motor therein, said patient compartment having a front wall and a floor and a pair of side walls;
a power supply cooperative with said patient compartment; and
a CT Computerized Tomography (CT) scanner positioned in said patient compartment and connected to said power supply so as to supply power to said CT scanner, said CT scanner being movable between a first position and a second position, said first position being rigidly affixed to said front wall of said patient compartment, said second position being spaced from said front wall, said patient compartment having a door on one of said pair of side walls, the apparatus further comprising:
a shelf mounted on said door so as to be extendable in an orientation transverse to said door and positioned outwardly of said patient compartment.

\* \* \* \* \*